US010273593B2

(12) United States Patent
Kwon et al.

(10) Patent No.: US 10,273,593 B2
(45) Date of Patent: Apr. 30, 2019

(54) POROUS ELECTRODES FOR SPECTROELECTROCHEMISTRY AND X-RAY STRUCTURE ANALYSES

(71) Applicant: UChicago Argonne, LLC, Chicago, IL (US)

(72) Inventors: Gihan Kwon, Lemont, IL (US); Jonathan D. Emery, Chicago, IL (US); In Soo Kim, Woodridge, IL (US); Alex B. Martinson, Naperville, IL (US); David M. Tiede, Elmhurst, IL (US)

(73) Assignee: UChicago Argonne, LLC, Chicago, IL (US)

( * ) Notice: Subject to any disclaimer, the term of this patent is extended or adjusted under 35 U.S.C. 154(b) by 187 days.

(21) Appl. No.: 15/221,167

(22) Filed: Jul. 27, 2016

(65) Prior Publication Data
US 2018/0031496 A1 Feb. 1, 2018

(51) Int. Cl.
*C25D 17/12* (2006.01)
*C25B 1/04* (2006.01)
*C25D 9/06* (2006.01)
*C25D 17/00* (2006.01)
*C25D 17/02* (2006.01)
(Continued)

(52) U.S. Cl.
CPC ............... *C25D 17/12* (2013.01); *C25B 1/04* (2013.01); *C25D 9/06* (2013.01); *C25D 17/00* (2013.01); *C25D 17/02* (2013.01); *C25D 21/12* (2013.01); *G01N 23/20* (2013.01); *G01N 2223/61* (2013.01)

(58) Field of Classification Search
CPC . C25B 1/04; C25D 17/12; C25D 9/04; G01N 2223/61; G01N 23/203
See application file for complete search history.

(56) References Cited

U.S. PATENT DOCUMENTS

| | | | |
|---|---|---|---|
| 2014/0093052 A1 | 4/2014 | Chupas et al. | |
| 2014/0102897 A1* | 4/2014 | Jerkiewicz | G01N 27/401 204/408 |
| 2016/0356921 A1* | 12/2016 | Shen | E21B 49/081 |

OTHER PUBLICATIONS

Borkiewicz, "Best Practices for Operando Battery Experiments: Influences of X-ray Experiment Design on Observed Electrochemical Reactivity," J. Phys. Chem. Lett., 6(11), pp. 2081-2085 (2015).
(Continued)

*Primary Examiner* — Mark R Gaworecki
(74) *Attorney, Agent, or Firm* — Foley & Lardner LLP

(57) ABSTRACT

An electrochemical cell that allows for in-situ structural characterization of amorphous thin film materials during the course of electrolysis using high-energy X-ray scattering (>50 keV). The compact and versatile cell employs a three-electrode configuration and minimizes X-ray scattering contributions from the cell, reference and counter electrodes, as well as the working electrode support. A large surface area working electrode has a physically robust support and is largely transparent to X-rays. This design, which utilizes a three-dimensional working electrode, also greatly improves the intensity and quality of the scattered signal compared to a two-dimensional working electrode. The in-situ cell can be used not only to investigate structural evolution during electrolysis using X-ray scattering (e.g. pair distribution function), but also to perform electrochemical potential-dependent structural analysis by extended X-ray absorption fine structure.

9 Claims, 13 Drawing Sheets

(51) Int. Cl.
*G01N 23/20* (2018.01)
*C25D 21/12* (2006.01)

(56) References Cited

OTHER PUBLICATIONS

Borkiewicz, et al., "The AMPIX electrochemical cell: a versatile apparatus for in situ X-ray scattering and spectroscopic measurements," J. Appl. Crystallogr., 45(6), pp. 1261-1269 (2012).
Danilovic, et al., "Activity-Stability Trends for the Oxygen Evolution Reaction on Monometallic Oxides in Acidic Environments," J. Phys. Chem. Lett., 5(14), pp. 2474-2478 (2014).
Du, et al., "Elucidating the Domain Structure of the Cobalt Oxide Water Splitting Catalyst by X-ray Pair Distribution Function Analysis," J. Am. Chem. Soc., 134(27), pp. 11096-11099 (2012).
Egami & Billinge, "Underneath the Bragg Peaks: Structural Analysis of Complex Materials," vol. 16 of Pergamon Materials Series, pp. 27-73 (2012).
Elam, et al., "Atomic Layer Deposition of Indium Tin Oxide Thin Films Using Nonhalogenated Precursors," J. Phys. Chem. C, 112(6), pp. 1938-1945 (2008).
Farrow, et al., "Intermediate-Range Structure of Self-Assembled Cobalt-Based Oxygen-Evolving Catalyst," J. Am. Chem. Soc., 135(17), pp. 6403-6406 (2013).
Gamoke, et al., "Nature of PO Bonds in Phosphates," The Journal of Physical Chemistry A, 113(19), pp. 5677-5684 (2009).
Hammersley, et al., "Two-dimensional detector software: From real detector to idealised image or two-theta scan," High Pressure Res., 14(4-6), pp. 235-248 (1996).
Ingham, et al., "In Situ Synchrotron X-ray Diffraction Experiments on Electrochemically Deposited ZnO Nanostructures," J. Phys. Chem. C, 112(38), pp. 14863-14866 (2008).
Jensen, et al., "Demonstration of thin film pair distribution function analysis (tfPDF) for the study of local structure in amorphous and crystalline thin films," IUCrJ, 2(5), pp. 481-489 (Sep. 2015).
Kanan & Nocera, "In Situ Formation of an Oxygen-Evolving Catalyst in Neutral Water Containing Phosphate and Co2 ," Science, 321(5892), pp. 1072-1075 (2008).
Kanan, et al., "Structure and Valency of a Cobalt-Phosphate Water Oxidation Catalyst Determined by in Situ X-ray Spectroscopy," J. Am. Chem. Soc., 132(39), pp. 13692-13701 (2010).
Klingan, et al., "Water Oxidation by Amorphous Cobalt-Based Oxides: Volume Activity and Proton Transfer to Electrolyte Bases," Chemsuschem, 7(5), pp. 1301-1310 (2014).
Koop, et al., "Electrochemical cell for in situ x-ray diffraction under ultrapure conditions," Rev. Sci. Instrum., 69(4), pp. 1840-1843 (1998).
Kordesch & Hoffman, "Electrochemical cells for in situ EXAFS," Nuclear Instruments and Methods in Physics Research, 222(1-2), pp. 347-350 (1984).
Laprade & Starcher, "The 2 Micron Pore Microchannel Plate: Development of the world's fastest detector," Burle Electro-Optics, Inc. (2001).
Ma, et al., "Double-Deck Inverse Opal Photoanodes: Efficient Light Absorption and Charge Separation in Heterojunction," Chem. Mater., 26(19), pp. 5592-5597 (2014).
Merte, et al., "Electrochemical Oxidation of Size-Selected Pt Nanoparticles Studied Using in Situ High-Energy-Resolution X-ray Absorption Spectroscopy," ACS Catalysis, 2(11), pp. 2371-2376 (2012).
Morcrette, et al., "In situ X-ray diffraction techniques as a powerful tool to study battery electrode materials," Electrochim. Acta, 47(19), pp. 3137-3149 (2002).
Newville, "IFEFFIT: interactive XAFS analysis and FEFF fitting," Journal of Synchrotron Radiation, 8(2), pp. 322-324 (2001).
Ocko, et al., "In situ x-ray reflectivity and diffraction studies of the Au(001) reconstruction in an electrochemical cell," Phys. Rev. Lett., 65(12), 1466-1469 (1990).
Proffen, et al., "Structural analysis of complex materials using the atomic pair distribution function—a practical guide," Z. Kristallogr., 218, pp. 132-143 (2003).
Qiu, et al., "PDFgetX2: a GUI-driven program to obtain the pair distribution function from X-ray powder diffraction data," J. Appl. Crystallogr., 37(4), p. 678 (2004).
Ravel & Newville, "Athena, Artemis, Hephaestus: data analysis for X-ray absorption spectroscopy using IFEFFIT," Journal of Synchrotron Radiation, 12(4), pp. 537-541 (2005).
Renner, et al., "Portable chamber for the study of UHV prepared electrochemical interfaces by hard x-ray diffraction," Rev. Sci. Instrum., 78(3), 033903 (2007).
Risch, et al., "Water oxidation by amorphous cobalt-based oxides: in situ tracking of redox transitions and mode of catalysis," Energy & Environmental Science, 8(2), pp. 661-674 (2015).
Risch, et al., "Water Oxidation by Electrodeposited Cobalt Oxides—Role of Anions and Redox-Inert Cations in Structure and Function of the Amorphous Catalyst," ChemSusChem, 5(3), pp. 542-549 (2012).
Robinson & O'Grady, "A transmission geometry electrochemical cell for in situ x-ray diffraction," Rev. Sci. Instrum., 64(4), pp. 1061-1065 (1993).
Sawyer, et al., "Electrochemistry for Chemists," John Wiley & Sons, Inc., p. 189 (1995).
Shi, et al., "Constructing inverse opal structured hematite photoanodes via electrochemical process and their application to photoelectrochemical water splitting," Phys. Chem. Chem. Phys., 15(28), pp. 11717-11722 (2013).
Surendranath, et al., "Electrolyte-Dependent Electrosynthesis and Activity of Cobalt-Based Water Oxidation Catalysts," J. Am. Chem. Soc., 131(7), pp. 2615-2620 (2009).
Surendranath, et al., "Mechanistic Studies of the Oxygen Evolution Reaction by a Cobalt-Phosphate Catalyst at Neutral pH," J. Am. Chem. Soc., 132(46), pp. 16501-16509 (2010).
Tamura, et al., "Structure of Active Adlayers on Bimetallic Surfaces:? Oxygen Reduction on Au(111) with Bi Adlayers," The Journal of Physical Chemistry B, 106(15), pp. 3896-3901 (2002).
Terban, et al., "Detection and characterization of nanoparticles in suspension at low concentrations using the X-ray total scattering pair distribution function technique," Nanoscale, 7, pp. 5480-5487 (2015).
Tidswell, et al., In situ x-ray-scattering study of the Au(001) reconstruction in alkaline and acidic electrolytes, Phys. Rev. B, 47(24), pp. 16542-16553 (1993).
Tuaev, et al., "In Situ Study of Atomic Structure Transformations of PtNi Nanoparticle Catalysts during Electrochemical Potential Cycling," ACS Nano, 7(7), pp. 5666-5674 (2013).
Veder, et al., "A flow cell for transient voltammetry and in situ grazing incidence X-ray diffraction characterization of electrocrystallized cadmium(II) tetracyanoquinodimethane," Electrochim. Acta, 56(3), pp. 1546-1553 (2011).
Virtanen, et al,. "In situ X-ray absorption near edge structure studies of mechanisms of passivity," Electrochim. Acta, 47(19), pp. 3117-3125 (2002).
Wang, et al., "In situ x-ray-diffraction and -reflectivity studies of the Au(111)/electrolyte interface: Reconstruction and anion adsorption," Phys. Rev. B, 46(16), pp. 10321-10338 (1992).
Watanabe, et al., "Design of an electrochemical cell for in situ XAS studies," J. Electron. Spectrosc. Relat. Phenom., 156-158, pp. 164-167 (2007).
Wiaderek, et al., "Comprehensive Insights into the Structural and Chemical Changes in Mixed-Anion FeOF Electrodes by Using Operando PDF and NMR Spectroscopy," J. Am. Chem. Soc., 135(10), pp. 4070-4078 (2013).

* cited by examiner

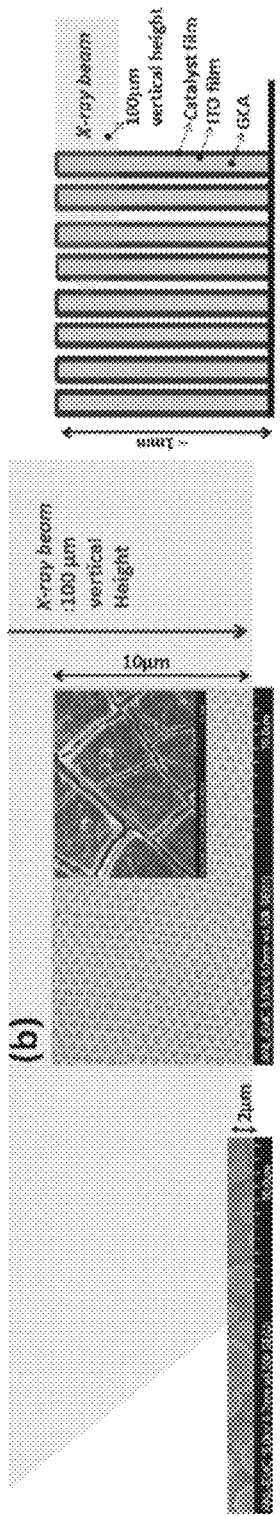
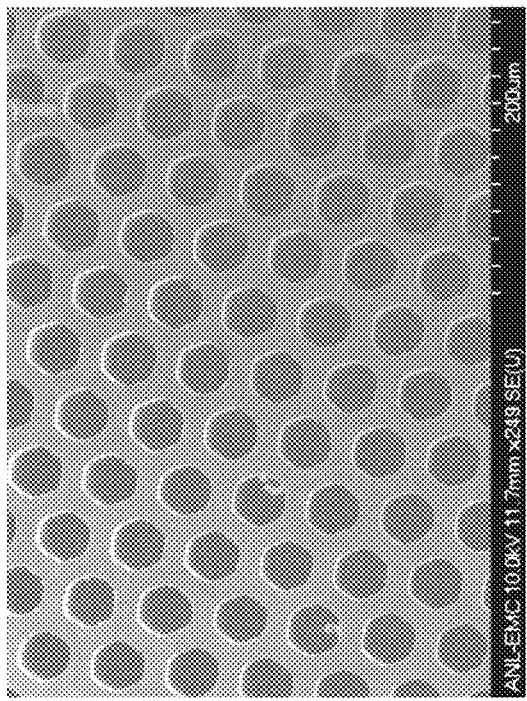
FIG. 1A
FIG. 1B
FIG. 1C
FIG. 1D

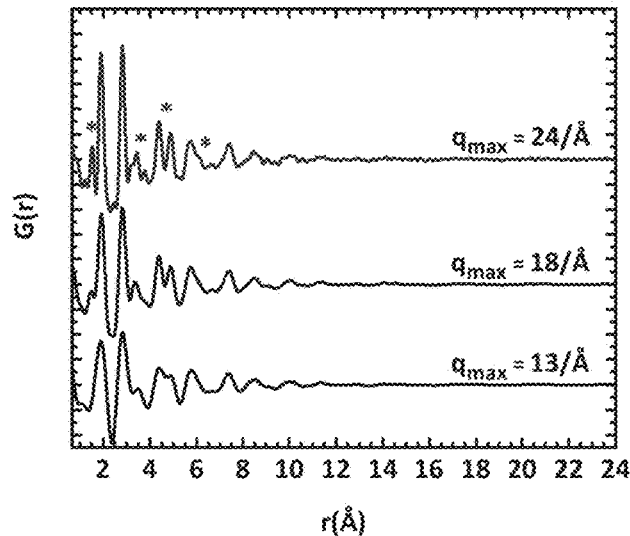
FIG. 3
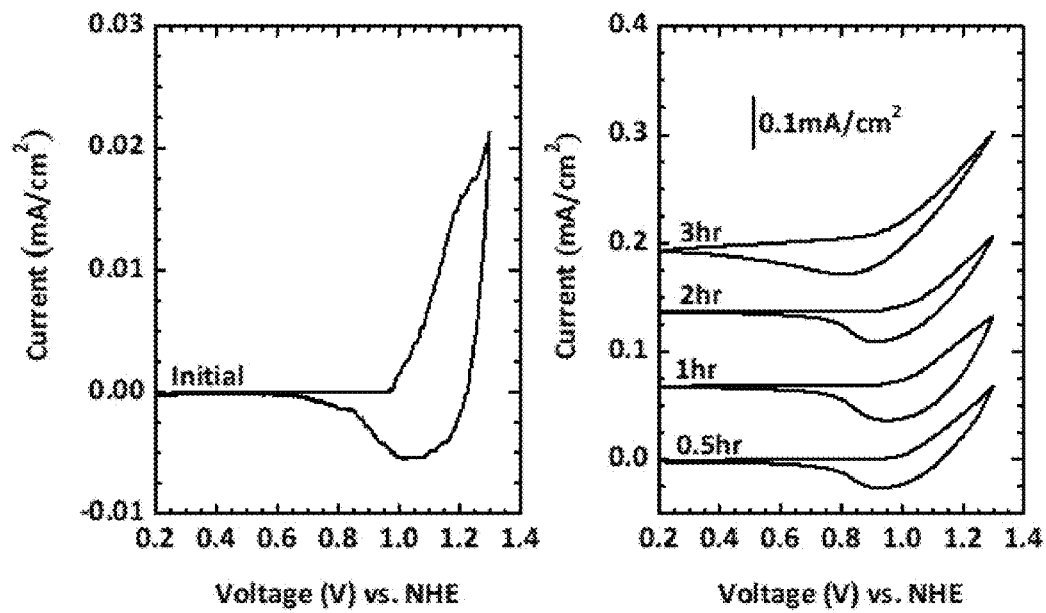
FIG. 4A
FIG. 4B

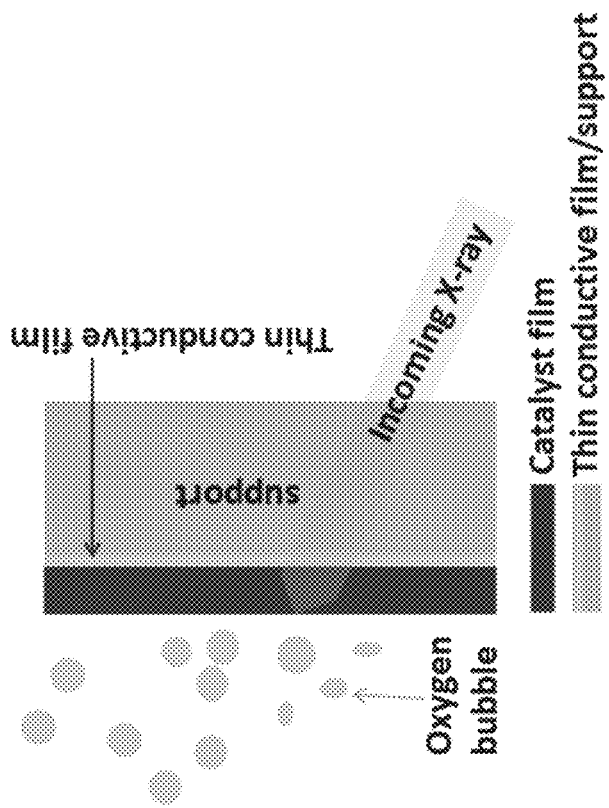
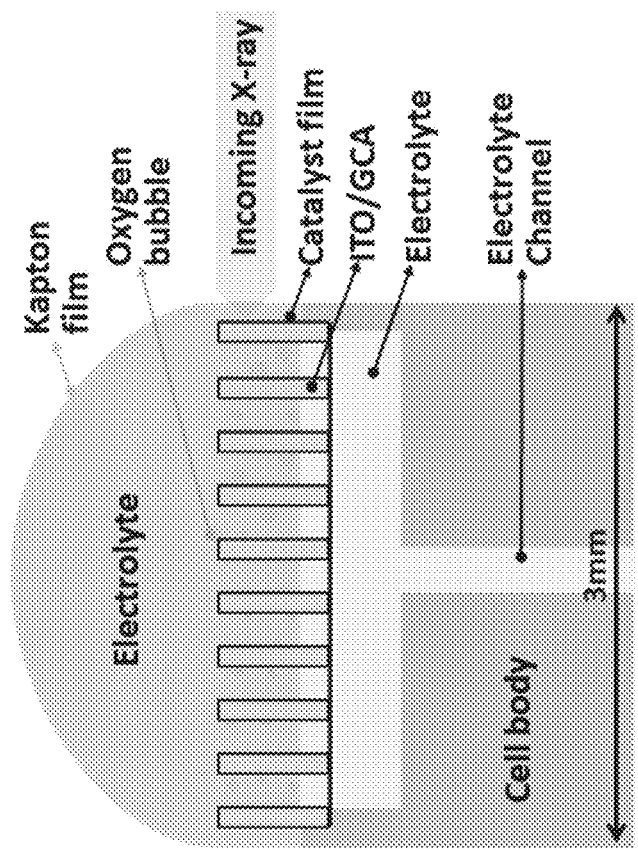
FIG. 7A
FIG. 7B

POROUS ELECTRODES FOR SPECTROELECTROCHEMISTRY AND X-RAY STRUCTURE ANALYSES

The United States Government claims certain rights in this disclosure pursuant to Contract No. W-31-109-ENG-38 between the United States Government and the University of Chicago, pursuant to DE-AC02-06CH11357 between the United States Government and U Chicago Argonne, LLC representing Argonne National Laboratory and/or by the U.S. Department of Energy, Office of Science, and Office of Basic Energy Sciences under Award Number DE-SC0001059.

TECHNICAL FIELD

The present disclosure relates generally to methods and systems for spectroelectrochemistry.

BACKGROUND

In-situ characterization of materials in various environmental conditions is a vitally informative technique in fields such as electrochemical energy storage, nanoparticle synthesis, and oxide thin film catalysis. In-situ characterization provides valuable information which is generally inaccessible to ex-situ experimentation, often clarifying phenomena which cannot be otherwise investigated. For electrodeposition processes specifically, it is valuable to know precisely the nature of the structure evolution of electrodeposited materials under electrochemically controlled conditions.

There is a great deal of literatures on electrochemical cell designs for various techniques including X-ray reflectivity and diffraction, high-energy X-ray scattering, and X-ray absorption spectroscopy. The reported in-situ X-ray characterization of thin amorphous water oxidation catalytic films is, to this point, only based on X-ray absorption. This method has typically been employed as an indirect probe of reaction surface because the formation of $O_2$ bubbles on working electrodes reduces the total counts of fluorescence signal. In addition, X-ray absorption spectroscopy cannot monitor film growth during electrolysis because discerning between the same elemental species in the electrolyte and film is impractical. High-resolution X-ray reflectivity and diffraction usually utilize hard X-rays (<30 keV), which is able to obtain structural information of amorphous materials but q range is too short to get well resolved pair distribution function. X-ray optics in this energy regime allow relatively straight-forward investigation of the top surface of the electrode or solid/liquid interface, but these techniques do not seriously take into account background subtraction, which is a critical factor in transforming scattering pattern to pair distribution function (PDF) for amorphous materials. Hard X-ray scattering provides high-quality scattering patterns from amorphous thin metal oxide films, but the range of momentum transfer ($q=k_f-k_i$, where $k_i$ and $k_f$ are the incoming and outgoing wave vectors, respectively) is typically too short (<15 Å$^{-1}$) to get sufficiently resolved pair distribution function (PDF).

The beam energy of X-ray absorption spectroscopy (XAFS)—including X-ray near edge structure (XANES) and Extended X-ray Absorption Fine Structure (EXAFS)—which is sensitive to the oxidation state and local coordination of element with short-range order, is close to X-ray absorption edge and could have strong potential to affect the measured results. X-ray beam-induced effect can be minimized by using high energy X-ray absorption. Scattering data from high-energy X-ray experiment will be converted to PDF to obtain the medium range of atomic pair distances which EXAFS cannot reach. PDF contributes immensely to the construction of structural information in complex and non-crystalline materials. Ultimately, however, both PDF and EXAFS are indispensable in understanding oxidation states and structural behavior during in-situ experiments. Here, we focus high energy X-ray scattering (HEXS) measurements, but the result of EXAFS measurement will be addressed as well. Up to now, the PDF technique has not been applied for the characterization of in-situ, electrode-supported amorphous thin metal oxide films (<2 μm) because of the need for a macroscopic scattering length (~1 mm) and the limited X-ray focus (≥10 μm) of the current high-energy X-ray technique.

SUMMARY

Embodiments described herein relate generally to an article of manufacture. The article comprises an in-situ cell. The cell has at least three electrodes including a working electrode (W.E.), a reference electrode (R.E.), and a cell electrode (C.E.). The cell further includes an electrolyte system including an electrolyte line and an electrolyte source in fluid communication with the in-situ cell. A film is disposed over the WE forming an WE electrolyte chamber.

Some embodiments relate to a method of characterizing a thin film within an electrochemical cell. The method comprises: depositing a thin film on a working electrode within the electrochemical cell; controlling the deposition at last in part by application of a current to a cell electrode in electrical contact with the working electrode; interacting the deposited thin film with an incident x-ray beam; measuring background scattering; and collecting CV data for the thin film.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIGS. 1A-1C are schematic illustrations of 100 μm tall X-ray beam interaction volumes of amorphous 2 μm thick CoPi thin films on various electrode structures. CoPi film deposited on (FIG. 1A) flat surface of 150 nm thin ITO on glass, on (FIG. 1B) 5-10 μm height inverse opal nanostructure, on (FIG. 1C) 50 nm thin ALD-ITO on 1 mm height GCA. Inset in FIG. 1B is inverse opal nanostructure made of 500 nm polystyrene bead. Inset in FIG. 1C CoPi deposited on 50 nm thin ALD-ITO coated GCA with 40 μm pores. The 100 μm tall X-ray beam was used for in-situ experiments and it fully interacts with 1 mm tall ITO/GCA. Only 15% of 100 μm vertical height X-ray beam is shown in FIG. 1A and FIG.

1B because the vertical size of X-ray beam is too large to compare CoPi on flat surface (FIG. 1A) and inverse opal nanostructures (FIG. 1B). FIG. 1D illustrates a photomicrograph of bare 40 um pore GCA (249× magnification)

FIG. 3. The dependence of the spectral quality of G(r) on $q_{max}$. G(r) was obtained from performing a Fourier transfer of the scattering data (S(q)) of the same CoPi powder dataset, but the different $q_{max}$ was selected for each plot. The asterisk (*) indicates highly resolved regions of G(r) possible with large $q_{max}$.

FIG. 4. A series of CVs collected from in-situ electrochemical cell during electrolysis. (a) Initial CV before and (b) CV during electrolysis. Scan rate was 5 mV/sec.

FIGS. 7A-7B Illustration of the indirect and direct detection of fluorescence signal of in-situ XAFS experiment. FIG. 7B is the side view of FIG. 2C.

Figure 1E:
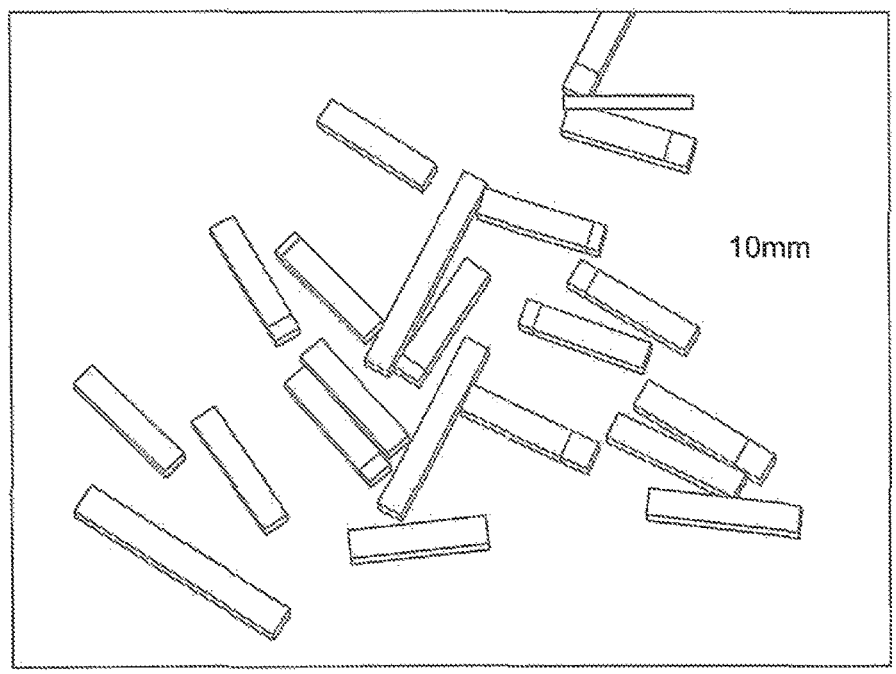
FIG. 1E illustrates the designed porous working electrode including ITO/GCAs (white and grey) and gold coated ITO/GCAs (yellowish color).
Figure 1F:
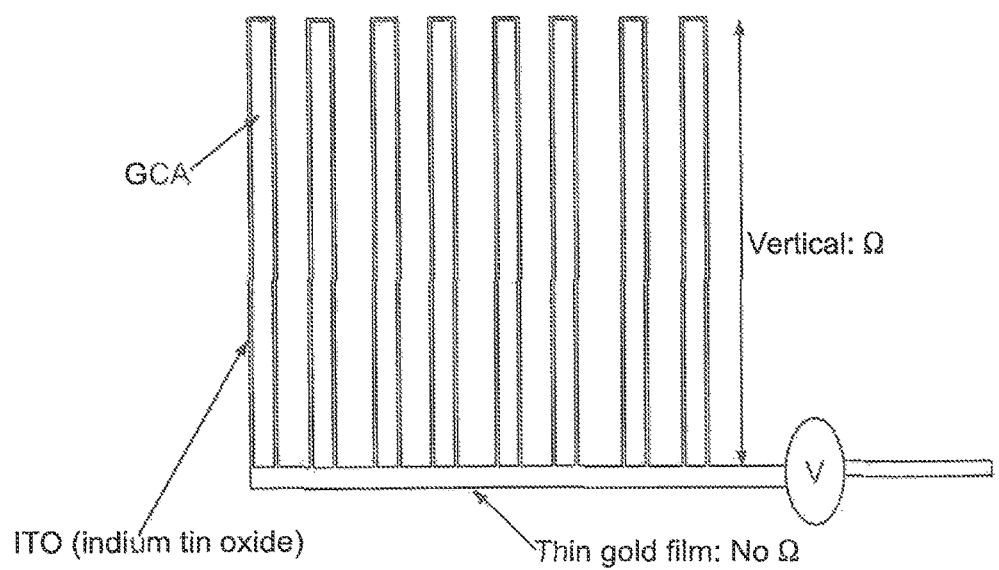
FIG. 1F illustrates the general structure of one embodiment shown in cross-section.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally the design of a versatile cell utilizing a three-dimensional electrode that is exceptionally useful in probing electrochemical processes in-situ using high-energy X-ray scattering and X-ray absorption spectroscopies.

Towards the goal of acquiring quality and highly resolved PDF from amorphous films relevant to electrochemical water oxidation, described herein is a macroscopic support which hosts micron-scale porous conductive materials to serve as electrodes for thin, amorphous, water-splitting catalytic films. Conventional, flat, amorphous thin films pose huge challenges due to their lack of long-range order and the small illuminated scattering area at high X-ray energy due to the thin film geometry and relatively unfocused X-ray beam. To circumvent this issue, high surface area supports were identified which are fully coincident with the large high-energy X-ray beam to be the best candidate substrate supports. One structure, inverse opal nanostructures, have often served as photoanodes for photoelectrochemical systems and should be suitable for in-situ work due to their three-dimensional high surface area and their absorption range of the sunlight.

However, these structures do not have enough mechanical strength, long-range continuity, or thickness (inverse opal films typically ≤10 μm) to be easily applied as supports in in-situ electrochemical HEXS. Instead, a glass capillary array (GCA) was chosen as the support material due to its large, open surface area and mechanical robustness. This support, in one embodiment, has a vertical dimension of 1.1 mm which allows use of the full, high-energy X-ray at the Argonne National Lab's (ANL) Advanced Photon Source (APS), which has a vertical dimension of 0.5 mm, for structural analysis of surface-supported materials. Its porous nature reduces scattering and absorption by the support itself, thereby increasing the incident X-ray flux on the thin film during in-situ deposition. Most importantly, the GCA provides porous structures with uniform pore sizes available in the 1 μm to 100 μm diameter range. The use of ALD and other techniques to coat these porous substrates with an electrically conductive surface layer creates a porous electrode geometry that has a surface area that can be chosen to be more than a thousand-fold higher than a conventional, single flat electrode design. Whereas at APS and other synchrotrons approximately 10 μm to 100 μm thick films are needed for high-energy X-ray scattering and PDF analysis of amorphous or molecular catalysts comprised of first row transition metals, embodiments of the present invention have demonstrated the ability to perform high-energy X-ray scattering and PDF analysis of amorphous cobalt oxide films that are electrocatalytically active and with film thickness of 50 nm (in alternative embodiments, no greater than 50 nm) using porous supports having a 40 µm pore diameter (in alternative embodiments, no greater than 40 nm). This unique architecture also facilitates X-ray Absorption Spectroscopy (XAS) to study the reaction surface directly in order to monitor the oxidation state and structural change of the water oxidation catalyst in-situ. Further the optically transparent nature of the porous GCA support allows for simultaneous analysis of surface electrochemistry using optical absorption spectroscopy.

An in-situ electrochemical cell utilizing a 3D working electrode for PDF which allows the study of structural evolution of amorphous films during aqueous electrolysis was developed. In one embodiment, one or more components may be fabricated by traditional means or by a 3-D printer. In a particular embodiment, a 3D printer is used to fabricate the intricate electrochemical cell to allow for precise arrangement of the three electrode setup. A glass capillary array (GCA) was used to serve as the substrate in the electrochemical cell to meet several requirements necessary for in-situ PDF and XAFS such as high surface area, for example >20 mm$^2$ surface area within the 0.5 mm×0.5 mm X-ray beam aperture, sufficient physical strength to be self-supporting and mechanically mountable, and have greater that 90% transparency for X-rays with energy of 50 keV and above. Other materials satisfying these requirements include carbon-based polymer materials made by lithography or printing techniques. The in-situ grown cobalt oxide film on GCA provides a scattering pattern of similar quality compared to that of an ex-situ grown bulk powder. One embodiment of an in-situ technique allows high-energy X-ray scattering and PDF analysis of 50 nm thin amorphous film of cobalt oxide. The setup not only enables the electrolytic growth an amorphous metal oxide films on an ITO-coated GCA but also allows acquisition of scattering patterns as XAFS signals during electrolysis or different potentials, which has not been thoroughly studied before. This cell offers a simple route for structural investigation of many electrodeposited thin amorphous catalytic films and will help provide clues to improve synthesis of water oxidation catalytic films.

Described below are examples illustrating certain embodiments as described.

EXPERIMENTAL PROCEDURES

A. Electrode Preparation

Designing a proper electrochemical cell for high-energy X-ray beam line applications requires several conditions. 1.) The electrochemical cell itself must work properly under reaction conditions. 2.) The host material, if 3D, has to be generally transparent to X-rays. 3.) The electrode—both support and conductor—should not create a large or complex background signal that complicates background subtraction. 4.) Finally, there exist serious constraints dictated by current high-energy X-ray optics, limiting the flux density of the incident beam. The 11-ID-B beamline at the APS, which is dedicated to HEXS for the study of the molecular structure, the minimum achievable beam size (before reducing flux) is about 500 µm×500 µm. In order to acquire the intense scattering signal from thin catalytic metal oxide film required for PDF, the X-ray illuminated film volume must be maximized and the background scattering from the electrode and the support must be minimized. The X-ray signal will scale with the intensity of the X-ray light source. The X-ray photon flux at the APS beamline 11-ID-B, used for experiements described herein, is $2.3 \times 10^{11}$ @ 58.66 keV. Accurate background subtraction is critical in PDF because Fourier transformation of scattering data without proper background subtraction can distort the structural interpretation. Cobalt phosphide and cobalt borate (CoPi and CoBi) thin films on Sn-doped indium oxide coated (ITO) glass were tested as well as on inverse opal nanostructures coated with atomic layer deposition (ALD)-grown ITO with HEXS. In both of these cases, acquiring a high quality scattering signal was not possible due to the limitation of small interaction volume with the incident X-ray beam, as shown in FIGS. 1A and 1B. The X-ray interaction volume for a 50 nm thin film supported on a planar electrode according to the interrogation geometry shown in FIG. 1A is $50 \times 10^{-6}$ mm$^3$. The interaction volume for the same film in the inventive cell using 40 µm diameter pores is $1500 \times 10^{-6}$ mm$^3$. The interaction volume scales larger with the larger surface areas with progressively smaller pore diameters.

The GCA volume interacts fully with X-ray, as shown in FIG. 1C. In the demonstration, the GCA was purchased from InCom, Inc. It is made of borosilicate glass, and possesses a 40 µm pores arrayed in a hexagonal honeycomb structure with a pore density of 60%. Flat, inverse opal nanostructures and GCA geometry possibly interact with 2%, 10%, and 100% due to the relative thicknesses, respectively (FIGS. 1A-1C). In order to utilize GCA as a working electrode (W.E., 10 mm long×2.5 mm wide×6 mm thick) support, a conductive layer must be deposited uniformly into the GCA pores. To this end, a 50 nm thick layer of ITO was deposited which was chosen to provide a conductive coating with a 50 Ω/cm resistance. The conductivity of the ITO layer can be controlled by choice of the ITO layer thickness. This ITO layer thickness was demonstrated to provide sufficient conductivity to support electrochemistry, and was thin enough to only minimally contribute to background scattering signal. For one embodiment, to decrease ITO film resistance further, 100 nm gold film was coated on bottom side of W.E. by evaporation.

B. Experimental Setup

Figure 2A:
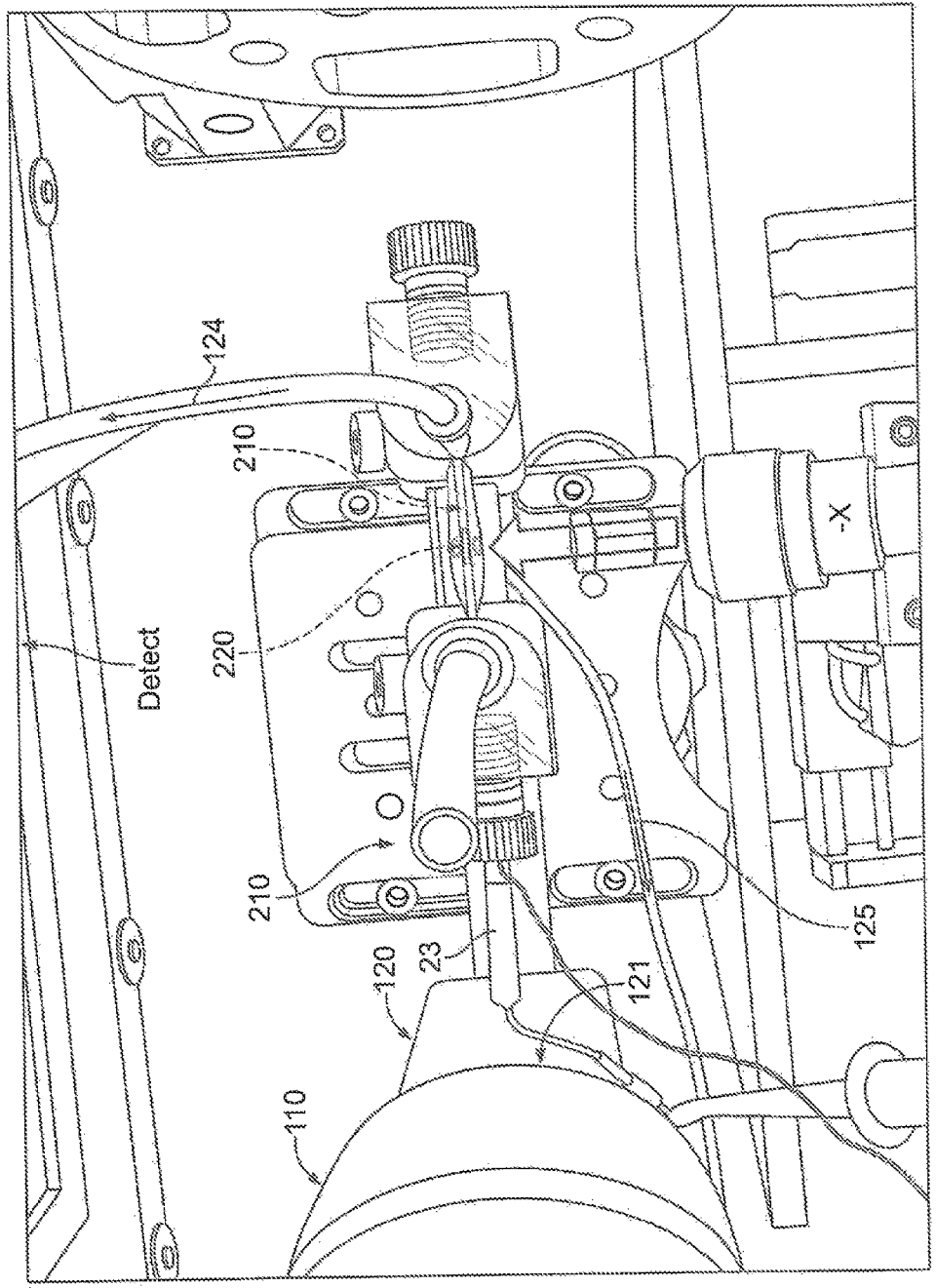
FIG. 2A illustrates an embodiment of an in-situ electrochemical cell on X-ray beam line.

FIG. 2A presents the picture of one embodiment of an in-situ electrochemical module 100 used for PDF measurements. The SEM image of bare 40 um pore GCA is shown at FIG. 1D and several ITO/GCAs and gold coated ITO/GCAs (yellowish colored) are shown at FIG. 1E. The main component of this module 100 is an electrolyte source 110, such as an electrolyte bottle, the in-situ cell 200 itself, which houses the working electrode (W.E.) 210, reference electrode (R.E.) 220, the cell electrode (C.E.). This embodiment utilizes a standard three electrode setup with the cell electrode providing control of the reaction at the working electrode by application of current. The electrochemical module 100 further includes, in one embodiment of FIG. 2A, a stirring system 120 for stirring the electrolyte in the electrolyte source 110. For example, the stirring system 120 may include a magnetic stirring apparatus 121. The electrolyte source 110 is in fluid communication with the cell 200, such as by one or more tubes 124. A pump 130, such as a syringe pump, may be provided in fluid communication with the cell 200 and the electrolyte source 110. The pump may be separate connected via pump tubes 125 The pump 130 can be placed anywhere in the system connected to the electrolyte source and cell. The system includes a C.E. 210, a W.E. 220, and a pair of R.E. 230.

In one example, the cell 200 was fabricated using a 3D printer (Objet30 Pro, Stratasys Ltd.) and used optically transparent VeroClear-RGD810 (Stratasys Ltd.) to permit monitoring of the inside of the cell during electrolysis or X-ray scattering. The W.E 220 was 50 nm of ALD-ITO on GCA connected with polyurethane/nylon insulated copper wire (8056, BELDEN). Silver paste (Cat. #12642-14, Electron Microscopy Science) was used to contact GCA and the copper wire and the assembly was dried in an oven. Chemical resistant epoxy (9340, Loctite) was applied to cover the silver paste and copper wire. Two built R.E.s 230 shown in FIG. 2B were used during measurements, constructed of a fluorinated ethylene propylene tube from McMaster-Carr, a porous Teflon frit from CH instruments, Inc., and thin silver wire from RE-5B of Bioanalytical Systems, Inc.

For one embodiment two identically constructed R.E. were oppositely positioned and placed 1 mm from the W.E. 220. The R.E.s 230 consisted of an electrochemically deposited AgCl film on 0.5 mm Ag wire that was inserted into a polytetrafluoroethylene (PTFE) 2 mm OD tube, filled with 3 M KCl electrolyte solution, and sealed with a 5 μm porous Teflon plug. The AgCl film on the Ag reference electrode was formed by electrochemical deposition from 0.1 M HCl with 0.5 V applied potential using a AgCl/Ag reference electrode and Pt wire counter electrode. The R.E. were stable for more than 10 hours of electrolysis. Chemically inert septa 223 were used to prevent electrolyte leaking and to hold the R.E. 230 and W.E. wire 221. A W.E. film 225, 7.5 μm thick kapton (NC0775341, Fisher Scientific) in the experiments descried, shown in FIG. 2B was used to cover the electrolyte on W.E. 220 region by applying a chemical-resistant epoxy (LOCTITE® 9340, McMaster-Carr). Other film 225 materials can be substituted, but Kapton is widely used because of the chemical inertness and stability to X-ray exposure. A broad range of film thicknesses are usable; the 7.5 μm thickness in the embodiment is minimizes X-ray scattering background and has high visible transparency compared to thicker films.

Figure 2B:
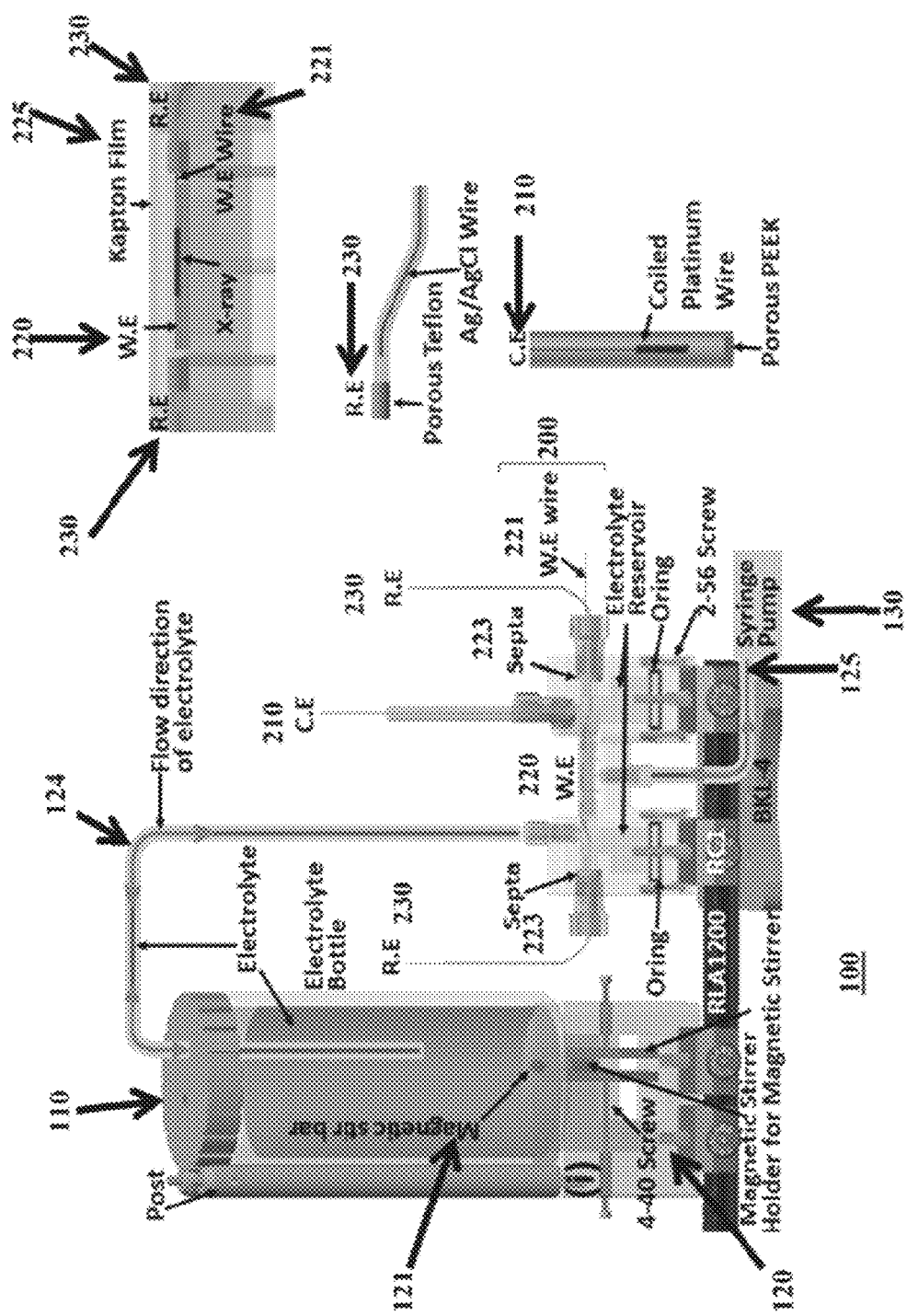
FIG. 2B illustrates another in-situ electrochemical cell assembly consisting of electrolyte bottle, cell body, (W.E., R.E., C.E., and the housing of magnetic stirrer. The incident direction of X-ray to GCA is perpendicular to pore direction shown in FIG. 1C, FIG. 2F and FIG. 7B.
Figure 2C:
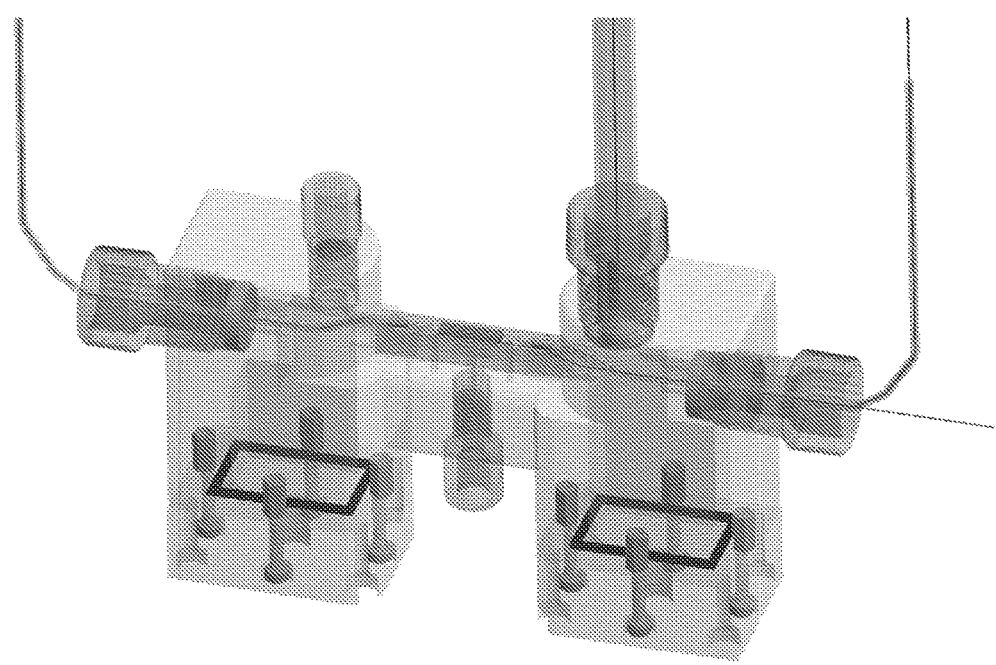
FIG. 2C illustrates one embodiment of a system with an electrochemical cell.
Figure 2D:
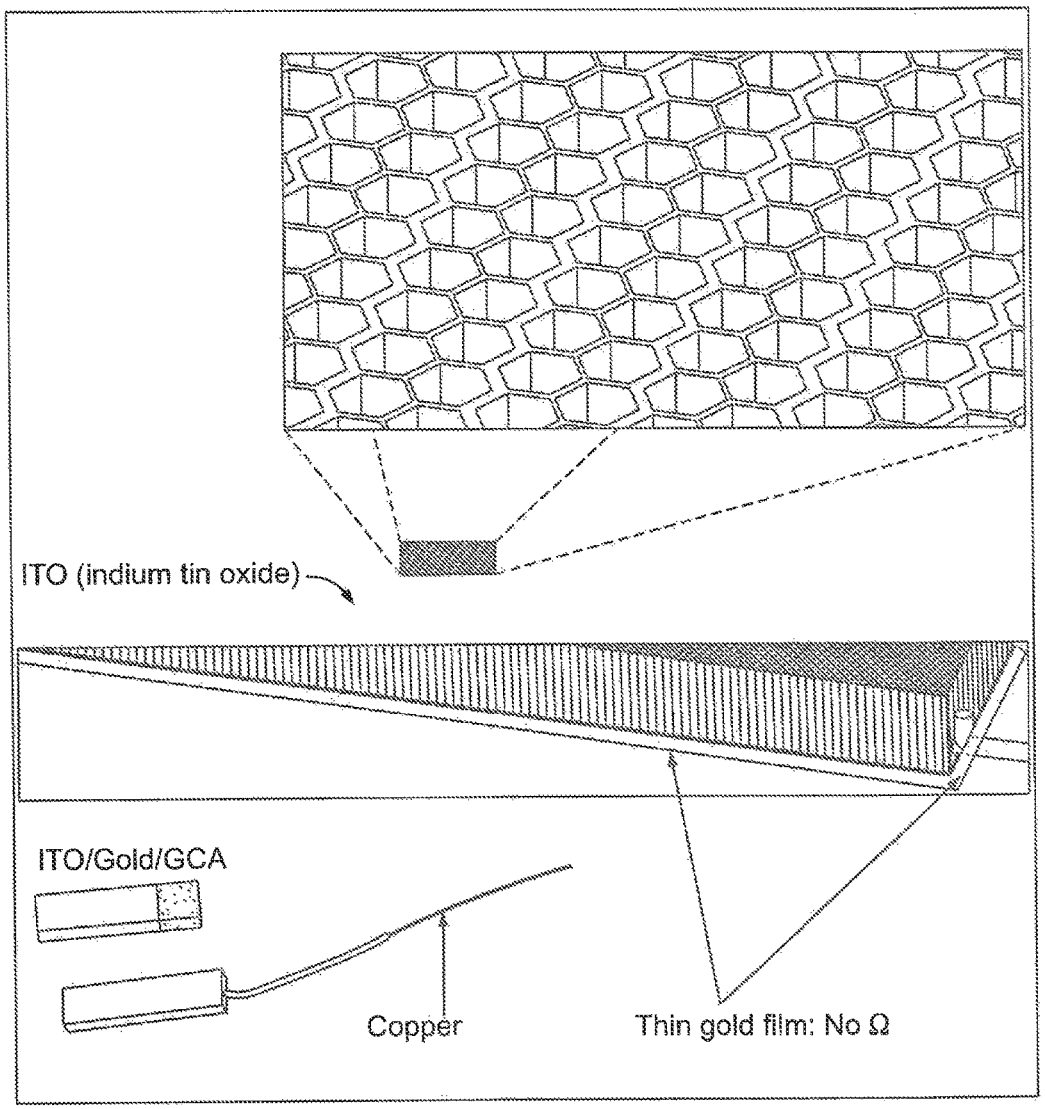
FIG. 2D illustrates an electrode of the system of FIG. 2C. The top inset illustrates a magnified view of the structure of the electrode.

In one embodiment, the W.E. region 224 has a cross-sectional shape, or electrolyte shape, atop the ITO/GCA electrode shown in FIG. 2B and FIG. 7B designed with a half-moon shape, or semi-ellipse shape, in order to avoid variation during electrolyte flow. This electrolyte shape also helps to collect a consistent scattering signal which makes background subtraction simple during PDF data analysis. All fittings that were in contact with electrolyte were made of PEEK (Polyether ether ketone) or PTFE (Polytetrafluoroethylene) except the body of the in-situ electrochemical cell itself. A coiled Pt wire, shown in FIG. 2B, was used as C.E. 210, and was housed in heat-shrinkable tubing (O.D: 5.7 mm and I.D: 5.2 mm) ZDS-L-190, ZEUS) and was compartmentalized using a porous PEEK disk (10 μm porosity, OC-803, IDEX Health&Science). The C.E. 210 can be formed from a range of other metals and materials. In common practice, Pt is selected because of minimal chemical reactivity, high conductivity, and readily regeneration.

During electrolysis, Hydrogen bubbles can cause the discontinuation of electrolyte in the housing of C.E. and this event may alter the measurement of the reaction current. In order to prevent this during electrolysis, internal diameter of the tube housing for the C.E. was chosen to be 5 mm or greater to allow facile release of hydrogen bubbles that are produced during anodic potential sweeps of the W.E. Before use, the printed in-situ cell was sonicated in a solution of 0.5 M NaOH solution in deionized water, and then rinsed using deionized water. This process was repeated several times to remove low-cross-linked support materials on the surface of the printed cell. The in-situ cell was mounted on a kinematic base (BKL-4, Newport), dovetail optical rail (RLA0600, THORLABS), and rail carrier (RC1, THORLABS). To flow electrolyte into the GCA channel, first an electrolyte-compatible syringe was pumped to remove bubbles through the entire cell and tubing. A syringe was mounted on a precise programmable syringe pump (NE-1000, New Era Pump Systems, Inc.) and syringe was moved back and forth to flow electrolyte continuously through cell the cell by a pre-programmed schedule in syringe pump. The arrow indicates the bidirectional flow of electrolyte seen in FIG. 2B. A magnetic stirrer (Model 1060 and 604KIT, Instech Laboratories, Inc.) was placed at the bottom of the electrolyte bottle to minimize precipitation of precursor and help to provide fresh electrolyte into cell. Phthalate-free TYGON tubing (Saint-Gobain SE-200, ⅛ inch OD, Fisher Scientific) was used to connect the electrolyte path. Importantly, this flow design helps purge oxygen bubbles forming on the W.E. to the electrolyte reservoir and avoids discontinuation of electrolyte on the W.E. surface.

C. Solution Preparation and Film Growth

For in-situ HEXS, electrolyte solutions of 0.1 M potassium phosphate (KPi, pH 7.0) containing 0.5 mM Co$(NO_3)_2 \cdot 6H_2O$ was prepared from mono- and dibasic-potassium phosphate ($KH_2PO_4$ and $K_2HPO_4$, Sigma-Aldrich) and boric acid ($H_3BO_3$, Sigma-Aldrich) with ultra-pure water (MilliQ, 18.2 MΩcm). The preparation of the electrolyte and cobalt oxide films (CoPi and CoBi) has previously been reported in the art. For ex-situ (or powder) HEXS, two cobalt oxide films, CoPi from 0.1 M KPI and CoBi from 0.1 M boric acid (KBi, pH 9.2), were electrodeposited on ITO/glass (CB-501N-1511, Rs=5–15Ω, Delta Technologies, Ltd). The pH of the electrolyte solution was adjusted using concentrated KOH (Sigma-Aldrich) solution. The deposited film on ITO/glass was directly scraped off from the ITO surface by glass capillary. Prior to performing in-situ EXAFS, CoPi film was grown over the course of two hours of electrolysis at 12 BM at the APS. After electrolysis, the used electrolyte for growing CoPi was replaced with $Co^{2+}$-free 0.1 M KPi solution due to difficulty to subtract the contribution of $Co^{2+}$ in electrolyte. After draining the used electrolyte, the assembly of the in-situ electrochemical cell was rinsed with MilliQ water for several times. Then $Co^{2+}$-free 0.1 M KPi solution was refilled into the cell and was circulated into the assembly of cell. Electrolysis of CoPi and CoBi was performed at a potential of 1.34V and 1.21V vs. NHE, respectively. To insure that the in-situ cell worked properly before starting the electrolysis, a CV was collected and compared to a CV which was taken from bulk electrolysis. CV was recorded in the range of 0.2-1.3 V vs. NHE with a scan rate of 5 mV/sec. A potentiostat (Epsilon, Bioanalytical Systems, Inc.) was used to perform all experiments. IR drop was not accounted for in any the electrochemical measurements.

For the detection sensitivity limit measurement, CoPi film was in-situ grown for 50 min at 1.34V vs. NHE. Then the scattering pattern of CoPi film was immediately collected after electrolysis.

D. X-Ray Data Acquisition and Processing

The current optics of high-energy incident X-rays (58.66 keV, λ=0.2114 Å) at 11ID-B at Advanced Photon Source (APS) of Argonne National Laboratory (11-ID-B is a dedicated pair-distribution-function (PDF) beamline operating at fixed energies of 58.66 and 86.7 keV.) allow only for an un-focused 500 μm×500 μm (vertical×horizontal) beam, which is sufficient for HEXS of materials which fill this X-ray beam cross-section, but could not be used to examine electrode supported thin-films comprise of first row transition metals with thickness less than 1 μm. To demonstrate the capabilities of the described systems and methods for HEXS characterization of thin film catalysts, the vertical beam size was slitted down to 100 μm×500 μm (vertical× horizontal) to probe the sample, and a 2D scattering pattern was collected using a Perkin-Elmer amorphous silicon detector (200 μm×200 μm/pixel, total size in width and height: 40.96 cm×40.96 cm). A sample-to-detector distance of 17.6 cm was used, calibrated using a $CeO_2$ powder pattern. The maximum q value accessible in this setup was $q_{max}=4\pi \sin(2\theta/2)/\lambda=24/Å$, where $2\theta$ is the scattering angle and $\lambda$ is the X-ray wavelength. The 2D X-ray scattering pattern was integrated to one-dimensional data using Fit2D software. Data was acquired at two vertically offset beam positions width X-ray beam as shown the side view in FIG. 2B. Background scattering patterns of dry ITO/GCA and electrolyte were subtracted from in-situ data, and data was corrected for X-ray polarization, sample absorption, and Compton scattering using the PDFgetX2 program. A detailed example of background subtraction has been previously described in the art.

For XAFS demonstration on the amorphous cobalt oxide film, CoPi, the XAFS spectra of cobalt K-edge were collected at 12 BM at APS. The X-ray energy was selected by Si (111) double crystals used in monochromator (detuning to 50% intensity) and was used to irritate the CoPi/ITO/GCA electrode directly at 45 degree of an angle. The XAFS spectra at the cobalt K-edge of cobalt foil and CoPi film were obtained by the fluorescence detection mode using a Canberra 13-element germanium solid state detector array with the fluorescence photon energy window set for the cobalt Kα emission. XAFS data analysis was performed with Athena package based on IFEFFIT.

Results and Discussion

According to the range of q as function of X-ray energy at a fixed distance between sample and detector, the range of q depends on the incoming energy of the X-ray, according to the well-known relation, $q=(4\pi/\lambda)\sin \theta$, where $\lambda$ is the X-ray wavelength and $\theta$ is the scattering angle. Because the X-ray wavelength decreases with energy, high energy X-ray allows a larger $q_{max}$ for a measured angle range, and provides a higher resolution pair distribution function, G(r). The dependence of G(r) on $q_{max}$ is clearly demonstrated in FIG. 3. G(r) with 24/Å of $q_{max}$ is well resolved between major peaks compared to the shorter range of q. This result is a good guide for in-situ experiment and is similar or better quality compared to the previous reports. The distance the sensor is positioned from the film is varied based upon the x-ray photon energy.

Cyclic voltammetry (CV) data is collected at a certain range of potential (0.2-1.3 V vs. NHE) to compare with CV data collected from the same film grown by bulk electrolysis. During the CV, a voltmeter monitors the applied potential between the W.E. and R.E. The CV before electrolysis in a KPi solution containing $Co^{2+}$ was recorded as shown in FIG. 4A. The oxidation transition of cobalt ion from $Co^{2+}$ to $Co^{3+}$ is not shown at anodic scan and is present at bulk electrolysis. The two broad peaks generally seen in the returning cathodic wave were not clearly observed due to no CoPi film on ITO. The onset potential is about 0.8 V, which is ~0.2 V higher than previously reported result. Difference in shape and peak potential of CVs is attributed to the intrinsic resistance of cell including R.E. which won't allow to perform bulk electrolysis. After acquiring initial CV, electrolysis was performed at 1.34 V vs. NHE and CVs were collected again after 0.5, 1, 2, and 3 hours.

The trend of current density in the CV curves in FIG. 4B roughly follows previous reports mentioning an increase of current density as electrolysis proceeds. The peak shape of cathodic wave becomes broaden and the peak position shifts to lower potentials in the course of time. The CV features are still useful to approximate the applied potential on W.E., which enables study of the structural change on applied potentials. Two wire connections on both sides of the GCA may decrease the resistance of the cell and help to improve CV quality.

Figure 5A:
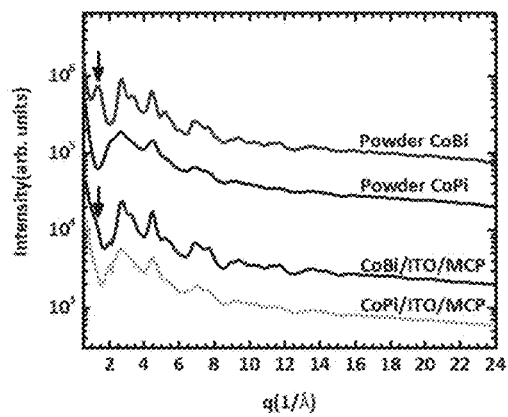
FIGS. 5A-5B show high-energy X-ray scattering data from (FIG. 5A) ex-situ CoPi and CoBi powders in glass capillaries as well as CoPi and CoBi films on ITO/GCA and (FIG. 5B) in-situ deposited CoPi film on ITO/GCA. All data were background subtracted (ITO, GCA, electrolyte, air). For CoBi and CoBi/ITO/GCA, the imperfections of background subtraction in FIG. 5A are observed at q~2.1/Å which is indicated by arrows at FIG. 5A.

FIGS. 5A-5D represent the comparison of scattering data from ex-situ and in-situ grown cobalt oxide water splitting catalyst films (CoPi and CoBi). In order to verify the usefulness of the GCA as a substrate for high-energy X-ray scattering, CoPi and CoBi were deposited on the whole surface on GCAs and their scattering signals were collected. As shown in FIG. 5A, the X-ray scattering patterns of CoPi and CoBi/ITO/GCA are similar to those of ex-situ powder scattering.

Figure 5B:
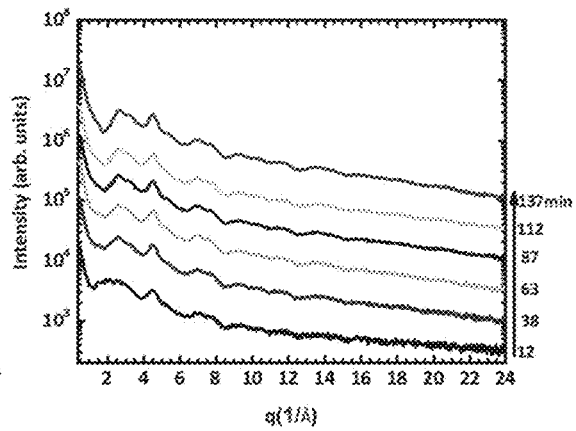

In FIG. 5A, the scattering pattern of CoBi/ITO/GCA at q=1.35/Å has a only small feature because the degree of layer stacking of CoBi on ITO/GCA is small. Qualitatively, FIG. 5A demonstrates that ITO/GCA can serve as a suitable substrate to grow and analyze the structure of a catalyst film. In terms of in-situ analysis, FIG. 5B shows that the scattering pattern of in-situ generated CoPi is similar to that of the ex-situ grown CoPi (FIG. 5A). The broadening of scattering pattern may be due to lack of order in the film at the initial stages (12 min) or the limitation of detection capability. At 38 minutes a more pronounced scattering signal was observed, similar to powder scattering, and after which none of the patterns changed for the rest of the experiment. No indication of contamination from the in-situ cell is observable in either the CV in FIGS. 4A-4B or scattering patterns in FIGS. 5A-5D.

Figure 5C:
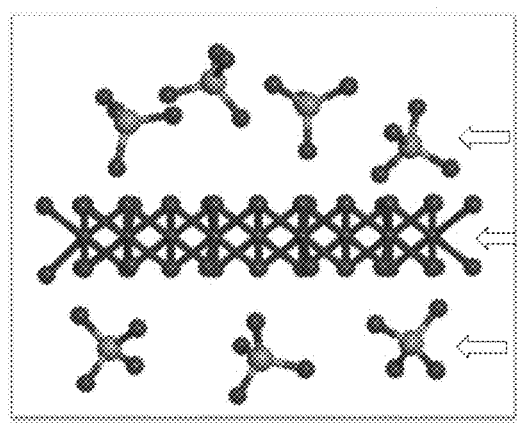
FIG. 5C illustrates the molecular structure of one embodiment which is the proposed structure determined by analysis of high-energy X-ray scattering data for the domains comprising an amorphous cobalt oxide water-oxidation catalyst that is formed by anodic (Eh>1.2 V versus the normal hydrogen electrode values, NHE) electrochemical deposition on the porous working electrode surface, and formed in the presences of 0.1 M sodium phosphate, pH 7.0 as the electrolyte.

FIG. 5C illustrates the molecular structure of one embodiment which is the proposed structure determined by analysis of high-energy X-ray scattering data for the domains comprising an amorphous cobalt oxide water-oxidation catalyst that is formed by anodic (Eh>1.2 V versus the normal hydrogen electrode values, NHE) electrochemical deposition on the porous working electrode surface, and formed in the presences of 0.1 M sodium phosphate, pH 7.0 as the electrolyte. The domain structure consists of a $Co(III)O_2$ single layer, with a structure analogous to that of $LiCoO_2$, but with restricted size, corresponding to 13 cobalt atoms as the average domain size. The figure illustrates the structure with cobalt atoms in blue, and oxygen atoms in red. The X-ray analysis of the amorphous domain further demonstrates distortions in the octahedral coordination geometry for cobalt atoms at the domain edge, and the presence of phosphate anions, $PO_4^{2-}$, that are disordered in structure, illustrated with phosphorous atoms in green, and oxygen atoms in red.

Figure 5D:
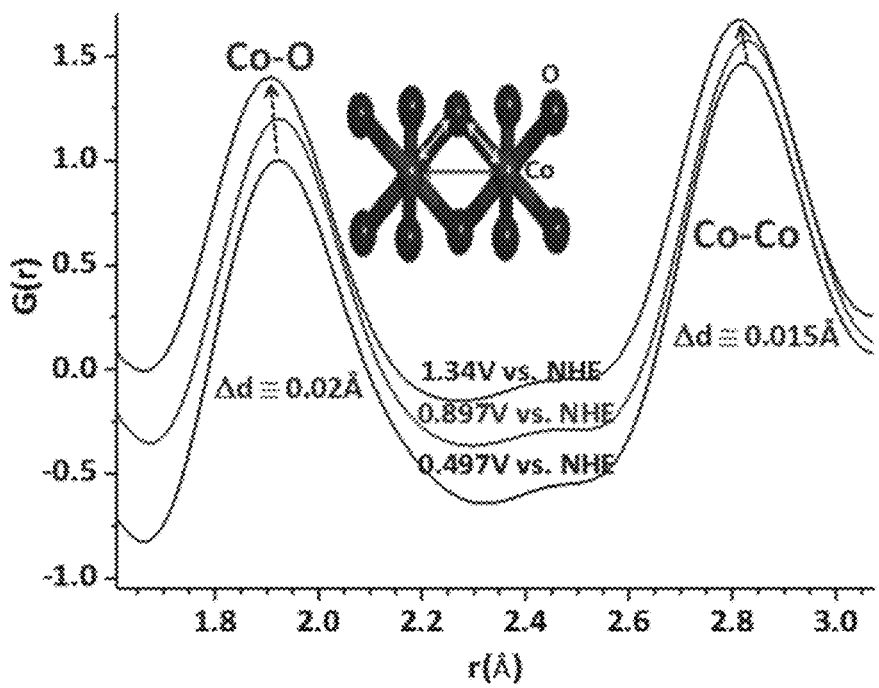
FIG. 5D illustrates use of porous electrode design for an analysis of electrocatalyst structure measured using high-energy X-ray scattering during an electrocatalytic processes.

FIG. 5D illustrates use of porous electrode design for an analysis of electrocatalyst structure measured using high-energy X-ray scattering during an electrocatalytic processes. Here, selected atom-pair distances are measured for the amorphous cobalt oxide water-oxidation catalysts film poised at three different electrochemical potentials, 0.497 V, 0.897 V, and 1.34 V versus the normal hydrogen electrode (NHE). The graph shows a selected region of the atomic pair distribution function, PDF, illustrating the change in the cobalt-oxygen bond length that is shifting between 1.91 angstrom to 1.89 angstrom with measurements at different applied electrochemical potential, and the corresponding changes in the Co—Co atom pair distances for cobalt atoms connected by di-µ-oxo bonding. The inset shows the structure related to these atom pair distance measurements.

Figure 6:
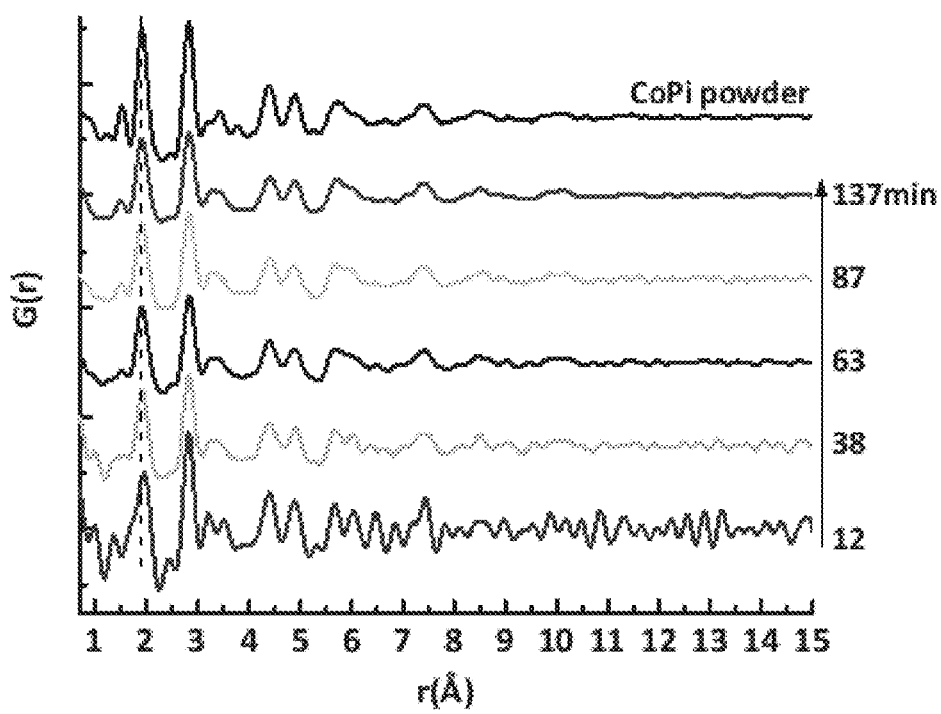
FIG. 6 PDF, G(r), measured for a CoPi powder scrapped off on ITO glass and measured CoPi in-situ film during electrolysis. G(r) of CoPi powder is a reference for comparison.

FIG. 6 showed the evolution of PDF during electrolysis of CoPi. G(r) data at 12 min has a some scatter due to relatively low statistics. Interestingly, the position of first peak (at r~2 Å), which indicates the distance of Co—O, shifts toward higher r at 12 min compared to the later time series.

The data in FIG. 6 also shows the structural evolution of P—O bonding peak over time. This peak gradually shifts toward 1.50 Å (which is still 0.02 Å shorter than that of powder) and becomes gradually pronounced with increasing electrolysis time. G(r) at 137 min is still not sharp like that of CoPi Powder but is comparable.

Current and new detection methods of in-situ XAFS study for water oxidation are represented in FIGS. 7A and 7B. The formation of oxygen bubbles at the potential of water oxidation drops fluorescence signal. Therefore the indirect method in FIG. 7A is often used for analyzing structural evolution at different electrochemical potentials. Conversely, in the direct method (FIG. 7B), the majority of bubbles in are generated at the inside surface of pores in GCA and not outside surface which X-ray will incident on. To obtain structural information on the reaction surface, X-ray beam in indirect method must access the reaction surface through the support, the thin conductive film such as ITO film, and the catalytic film. The thickness of support and catalyst film must then be sufficiently thin. The direct method in FIG. 7B allows to probe reaction surface directly with less loss of fluorescence signal compared to the indirect method.

Figure 8:
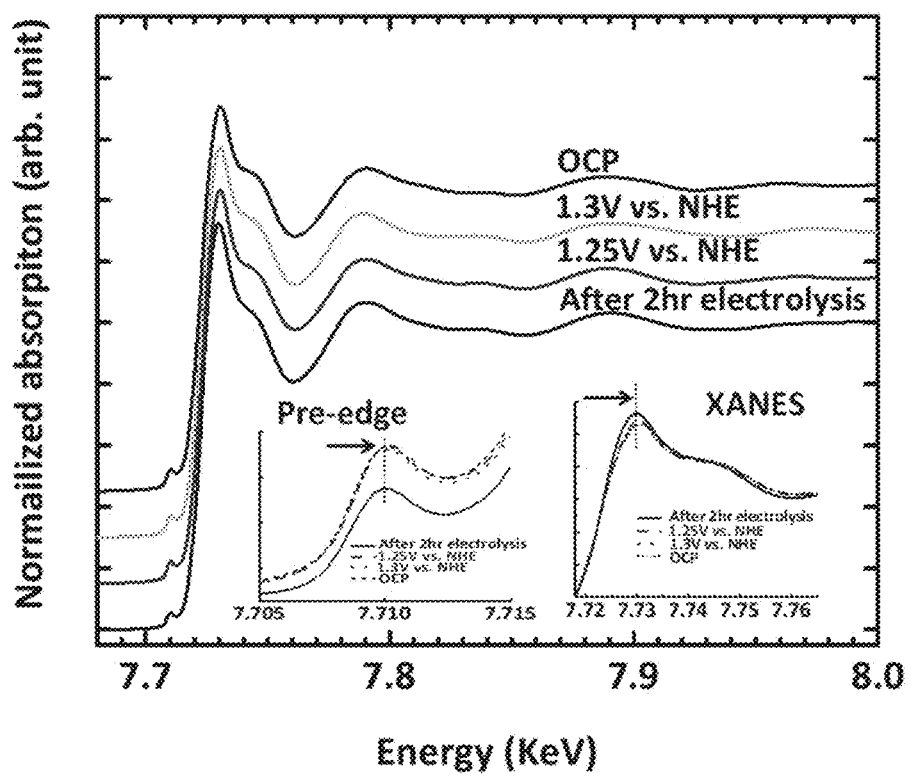
FIG. 8 In-situ Co K-edge XAFS spectra at various applied potentials. The insets in FIG. 8 magnify the region of pre-edge and XANES. The sequence of XAFS spectra was after 2 hours of electrolysis, 1.25 V, 1.3 V and open circuit potential (OCP), respectively.
Figure 9A:
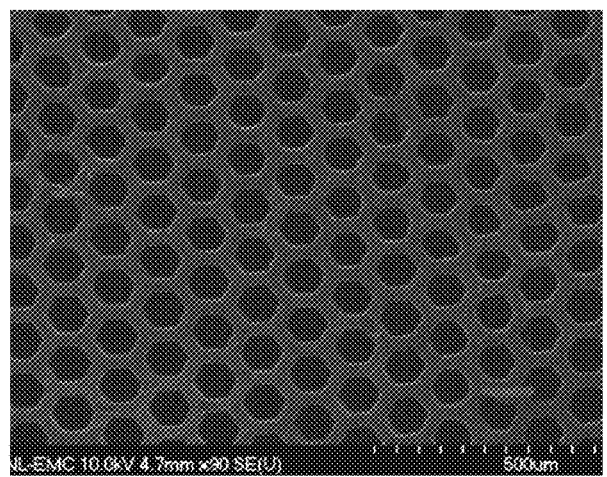
FIG. 9A SEM images of the electrodeposited CoPi catalyst film deposited during the in-situ high-energy X-ray scattering experiment.
Figure 9B:
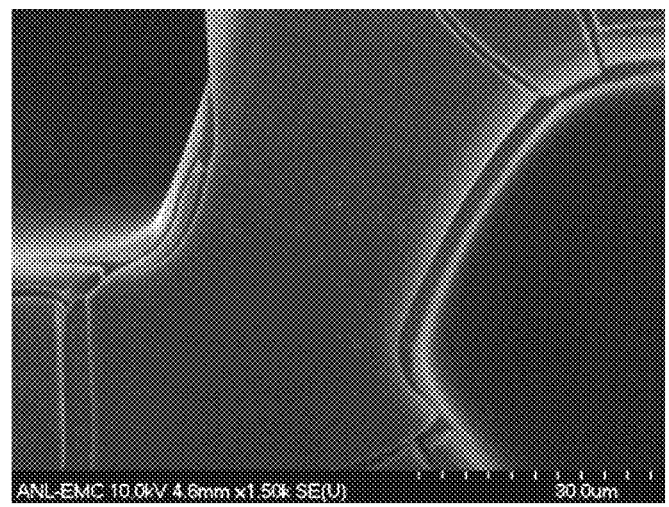
FIG. 9B Magnified image of FIG. 9A.
Figure 9C:
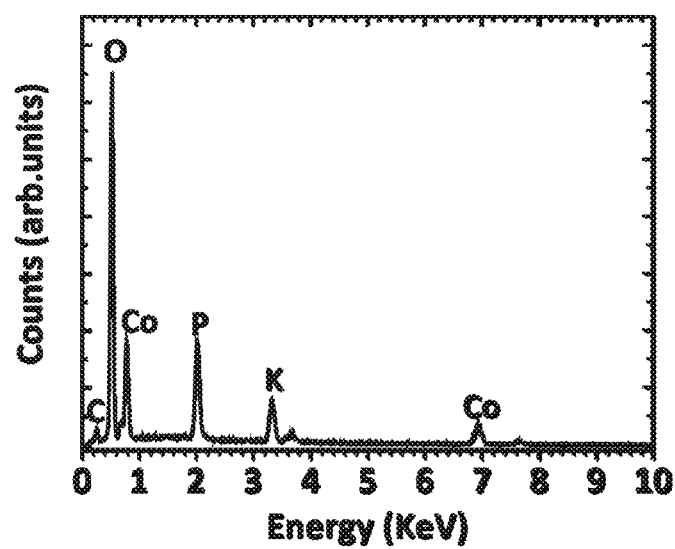
FIG. 9C EDX plot of FIG. 9A acquired at 12 kV. Carbon, Oxygen, phosphorous, and potassium are originated from $K\alpha$. Co at 6.929 keV and at 0.776 keV is originated from $K\alpha$ and $K\beta$ respectively.

FIG. 8 presents the in-situ measurement of XAFS under different potentials with 2 µm thick CoPi film on ITO/GCA electrode. The X-ray beam irradiates on the side of ITO/GCA to avoid the drop of the intensity of florescence signal as described at 7B. Recently, results of in-situ XAFS measurements of thin CoPi (≤40 nm, 2.4 nm and 480 nm) were reported but were not performed with micron thick film (≤2 µm). The peak positions of pre-edge and white line in insets shown in FIG. 8 were shifted to higher energy compared to the peak position of after 2 hr electrolysis. The position of main edge (7.709 keV) wasn't shifted toward to higher energy compared to the reported results. This may be attributed to thick film. After deposition and characterization, the film thickness was equivalent to 2 µm which is much thicker than that of the reported.

Scanning electron microscopy (SEM) images of in-situ grown CoPi on ITO/GCA are shown in FIG. 5B and 8 after the in-situ HEXS and XAFS experiment. The morphology of the CoPi film has no observable spheres or particles in the thin film morphology because mono- and dibasic KPi buffers were used. The CoPi film covers the whole surface area of the ITO/GCA, and the film thickness is about 2 µm (FIG. 2B). The crack in the film was caused by drying and has also been observed elsewhere. The film composition was assayed by energy-dispersive X-ray spectroscopy (EDX). The Co:P:K ratio of the composition of the film was 3:1:0.7, which is similar to previous reports.

Figure 10A:
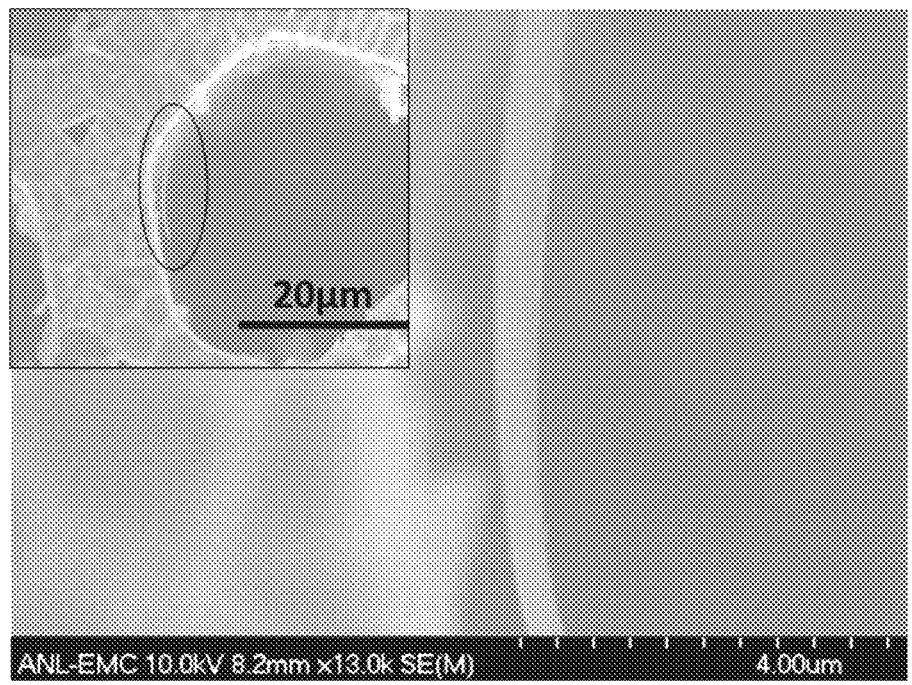
FIG. 10A SEM image of CoPi film on ITO/GCA. Film thickness is about 400 nm after 50 min electrolysis and FIG. 10B scattering patterns of 8 and 50 min electrolysis. Image within FIG. 10A magnified from circle in inset. Film thickness is 400 nm. Grey dash line in FIG. 10B is for background guidance. Scattering intensities indicated by arrows were used to estimate the capability of detection.

To evaluate a possible detection limit of the in-situ cell under these experimental conditions, the same experiment as shown in FIG. 5B was repeated to obtain scattering patterns at 8 and 50 min (FIG. 10A). The thickness of the CoPi film was 400 nm as measured by SEM and shown in FIG. 10A.

Figure 10B:
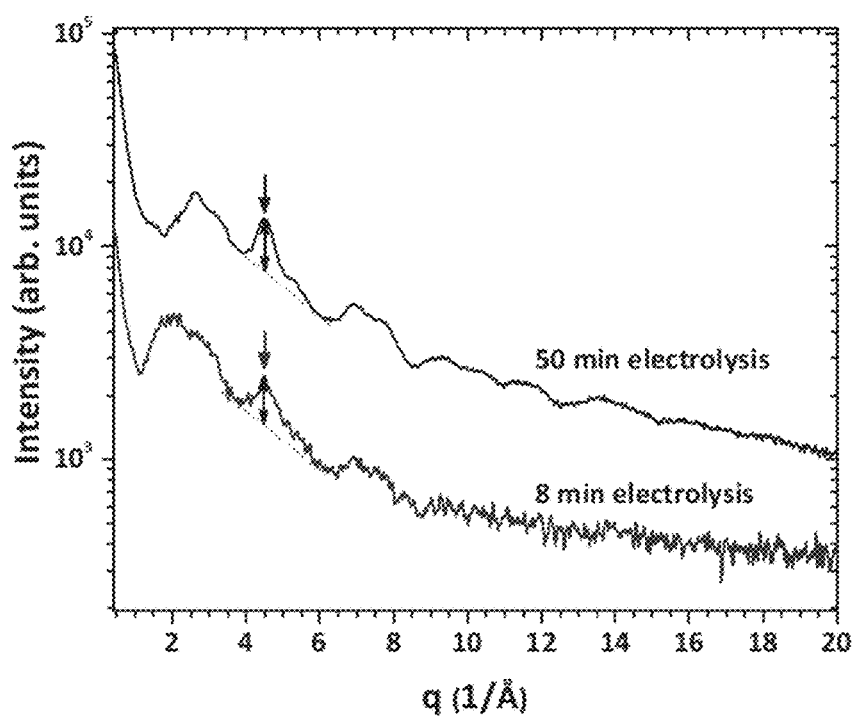

To estimate the detection limit from these scattering intensities, peak scattering intensities at q=4.5/Å for 8 min and 50 min depositions (indicated by two arrows in FIG. 10B) were compared. Under the assumption that the film growth rate is constant and that the 50 min film is 400 nms, we find that the 8 min film is ~70 nm thick. At this point, the signal to background ratio is ~2452 counts/2 min exposure, which is believed to define as an approximate conservative lower bound detection limit for PDF analysis.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An article of manufacture comprising:
   an in-situ cell comprising:
   at least three electrodes including a working electrode (W.E.), a reference electrode (R.E.), and a cell electrode (C.E.), the C.E. configured to receive current and in electrical communication with the W.E. whereby electrodeposition within the in-situ cell occurs at the W.E., the R.E. in electrical communication with the W.E. and configured to measure potential therebetewen;
   the W.E. comprising a glass capillary array having a conformal conductive layer;
   a film over the W.E., the W.E. and film defining a W.E. electrolyte region;
   an electrolyte system including an electrolyte line and an electrolyte source in fluid communication with the in-situ cell.

2. The article of manufacture of claim 1, wherein the glass capillary array is a microporous glass capillary array having pores with a diameter of 40 µm or less and at least a 20 mm$^2$ surface area.

3. The article of manufacture of claim 2, wherein the conformal conductive layer is less than 70 nm thick.

4. The article of manufacture of claim 1, wherein the W.E. further comprises a metallic layer deposited on the glass capillary array opposite the conductive layer.

5. The article of manufacture of claim 1, wherein the conformal conductive layer is less than 50 nm thick.

6. The article of manufacture of claim 1, wherein the W.E. electrolyte region has a cross-section shape selected from half-moon, semi-elliptical, and semi-circular.

7. The article of manufacture of claim 1, wherein the film is 7.5 µm thick.

8. The article of manufacture of claim 1, wherein the electrolyte system further including a stirrer associated with the electrolyte source and configured to stir electrolyte in the electrolyte source.

9. The article of manufacture of claim 1, wherein the electrolyte system further comprises a pump.

* * * * *